(12) United States Patent
Liu et al.

(10) Patent No.: US 11,136,545 B2
(45) Date of Patent: Oct. 5, 2021

(54) **RECOMBINANT *BACILLUS SUBTILIS* AND USE THEREOF**

(71) Applicant: JIANGNAN UNIVERSITY, Wuxi (CN)

(72) Inventors: Long Liu, Wuxi (CN); Xueqin Lv, Wuxi (CN); Guocheng Du, Wuxi (CN); Jianghua Li, Wuxi (CN); Jian Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 119 days.

(21) Appl. No.: 16/223,206

(22) Filed: Dec. 18, 2018

(65) Prior Publication Data

US 2020/0071778 A1  Mar. 5, 2020

(30) Foreign Application Priority Data

Aug. 28, 2018  (CN) .......................... 201810990055.X (51) Int. Cl.
| | |
|---|---|
| *C12P 19/26* | (2006.01) |
| *C12N 1/20* | (2006.01) |
| *C12N 9/10* | (2006.01) |
| *C12R 1/125* | (2006.01) |

(52) U.S. Cl.
CPC .............. *C12N 1/205* (2021.05); *C12N 1/20* (2013.01); *C12N 9/1029* (2013.01); *C12N 9/1096* (2013.01); *C12R 2001/125* (2021.05); *C12Y 203/01004* (2013.01); *C12Y 206/01016* (2013.01)

(58) Field of Classification Search
None
See application file for complete search history.

(56) References Cited

U.S. PATENT DOCUMENTS

| | | | |
|---|---|---|---|
| 2010/0047266 A1* | 2/2010 | Haynes | A61K 39/155 424/186.1 |
| 2017/0183686 A1* | 6/2017 | Khvorova | C12N 15/88 |
| 2020/0071778 A1* | 3/2020 | Liu | C12N 9/1096 |
| 2020/0109183 A1* | 4/2020 | Wiklander | A61P 43/00 |

* cited by examiner

*Primary Examiner* — Richard C Ekstrom
(74) *Attorney, Agent, or Firm* — SZDC Law PC (57) ABSTRACT

The invention provides a recombinant *Bacillus subtilis*, construction method and use thereof, wherein the cell's own FMMs are used as a space scaffold, and a multi-enzyme complex is constructed from specific marker proteins FloA and FloT, such that an artificial substrate channel is formed, and the cell metabolic burden is effectively reduced. The recombinant *Bacillus subtilis* of the invention can efficiently synthesize GlcNAc without affecting cell life activity, and can also limit the toxic intermediate metabolite GlcN-6-P near the plasma membrane to reduce or eliminate its inhibition on cell activity. In the process of shaking flask fermentation using complex medium, the yield of acetyl glucosamine of the control strain BSG-C was only 0.45 g·L$^{-1}$, while that of BSG-AT, BSG-ATP, BSG-ATPB increased to 5.29 g·L$^{-1}$, 6.22 g·L$^{-1}$ and 8.48 g·L$^{-1}$ respectively. The construction method of recombinant *Bacillus subtilis* is simple, easy to use and has a good application prospect.

6 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Linker

<400> SEQUENCE: 1
```

```
ggtggcggtg gaagcggcgg tggcggaagc ggcggtggcg gcagc            45
```

<210> SEQ ID NO 2
<211> LENGTH: 717
<212> TYPE: DNA
<213> ORGANISM: Artificial Sequence
<220> FEATURE:
<223> OTHER INFORMATION: EGFR Gene

<400> SEQUENCE: 2

```
atgggtaagg gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaagcttc ctgttccttg gccaacactt   180
gtcactactc ttacttatgg tgttcaatgc ttttcaagat acccagatca tatgaagcgg   240
cacgacttct tcaagagcgc catgcctgag ggatacgtgc aggagaggac catcttcttc   300
aaggacgacg gaactacaa  gacacgtgct gaagtcaagt tgagggaga  cccctcgtc    360
aacagaatcg agcttaaggg aatcgatttc aaggaggacg gaaacatcct cggccacaag   420
ttggaataca actacaactc ccacaacgta tacatcatgg cagacaaaca aaagaatgga   480
atcaaagtta acttcaaaat tagacacaac attgaagatg aagcgttca  actagcagac   540
cattatcaac aaaatactcc aattggcgat ggccctgtcc ttttaccaga caaccattac   600
ctgtccacac aatctgccct ttcgaaagat cccaacgaaa agagagacca catggtcctt   660
cttgagtttg taacagctgc tgggattaca catggcatgg atgaactata caaataa     717
```

<210> SEQ ID NO 3
<211> LENGTH: 503
<212> TYPE: DNA
<213> ORGANISM: Artificial Sequence
<220> FEATURE:
<223> OTHER INFORMATION: Zeocin Resistant Gene

<400> SEQUENCE: 3

```
tagagatacc gttcgtatag catacattat acgaagttat cttgatatgg cttttatat    60
gtgttactct acatacagaa aggaggaact aaacatggcc aagttgacca gtgccgttcc   120
ggtgctcacc gcgcgcgacg tcgccggagc ggtcgagttc tggaccgacc ggctcgggtt   180
ctcccgggac ttcgtggagg acgacttcgc cggtgtggtc cgggacgacg tgaccctgtt   240
catcagcgcg gtccaggacc aggtggtgcc ggacaacacc ctggcctggg tgtgggtgcg   300
cggcctggac gagctgtacg ccgagtggtc ggaggtcgtg tccacgaact ccgggacgc    360
ctccgggccg gccatgaccg agatcggcga gcagccgtgg gggcgggagt tcgccctgcg   420
cgacccggcc ggcaactgcg tgcacttcgt ggccgaggag caggactgaa taacttcgta   480
tagcatacat tatacgaacg gta                                           503
```

<210> SEQ ID NO 4
<211> LENGTH: 1133
<212> TYPE: DNA
<213> ORGANISM: Artificial Sequence
<220> FEATURE:
<223> OTHER INFORMATION: Chloromycetin Resistnat Gene

<400> SEQUENCE: 4

```
gtaccgttcg tatagcatac attatacgaa gttatcggaa tggacgatcg gcaatagtta    60
cccttattat caagataaga aagaaaagga ttttcgcta  cgctcaaatc ctttaaaaaa   120
```

```
acacaaaaga ccacattttt taatgtggtc ttttattctt caactaaagc acccattagt        180
tcaacaaacg aaaattggat aaagtgggat attttaaaa tatatattta tgttacagta         240
atattgactt ttaaaaaagg attgattcta atgaagaaag cagacaagta agcctcctaa        300
attcacttta gataaaaatt taggaggcat atcaaatgaa ctttaataaa attgatttag       360
acaattggaa gagaaaagag atatttaatc attatttgaa ccaacaaacg acttttagta      420
taaccacaga aattgatatt agtgttttat accgaaacat aaaacaagaa ggatataaat      480
tttaccctgc atttattttc ttagtgacaa gggtgataaa ctcaaataca gcttttagaa      540
ctggttacaa tagcgacgga gagttaggtt attgggataa gttagagcca ctttatacaa      600
tttttgatgg tgtatctaaa acattctctg gtatttggac tcctgtaaag aatgacttca      660
aagagtttta tgatttatac ctttctgatg tagagaaata taatggttcg gggaaattgt      720
ttcccaaaac acctatacct gaaaatgctt tttctctttc tattattcca tggacttcat      780
ttactgggtt taacttaaat atcaataata atagtaatta ccttctaccc attattacag      840
caggaaaatt cattaataaa ggtaattcaa tatatttacc gctatcttta caggtacatc      900
attctgtttg tgatggttat catgcaggat tgtttatgaa ctctattcag gaattgtcag      960
ataggcctaa tgactggctt ttataatatg agataatgcc gactgtactt tttacagtcg     1020
gttttctaaa acgatacatt aataggtacg aaaaagcaac ttttttttgcg cttaaaacca     1080 gtcataccaa taacttaaat aacttcgtat agcatacatt atacgaacgg tag            1133
```

RECOMBINANT *BACILLUS SUBTILIS* AND USE THEREOF

This application claims priority to Chinese Patent Application No. 201810990055.X, filed on Aug. 28, 2018, which is incorporated by reference for all purposes as if fully set forth herein.

FIELD OF THE INVENTION

The present invention relates to the field of genetic engineering, and more particularly to a recombinant *Bacillus subtilis*, construction method and use thereof.

DESCRIPTION OF THE RELATED ART

Acetylglucosamine is the synthetic precursor of glycosaminoglycan disaccharide unit in human body, which plays an important role in repairing and maintaining the function of cartilage and joint tissue. Therefore, acetylglucosamine is widely added in drugs and nutritional diets to treat and repair joint injury. In addition, acetylglucosamine is also widely used in cosmetics and pharmaceuticals. Currently acetyl glucosamine is mainly produced by chitin in shrimp shell or crab shell. However, the waste liquid produced by this method is serious to the environment, and the obtained product is easy to cause an allergic reaction, and thus is not suitable for the people with seafood allergy.

*Bacillus subtilis* is widely used as a host to produce food enzymes and important nutritional chemicals. Its products are certified as GRAS (Generally Regarded as Safe) safety grade by FDA.

In the process of natural evolution, microorganisms mainly form multi-enzyme complex and substrate channels to prevent the toxic intermediate metabolites from spreading to the cytoplasm, and improve the catalytic efficiency of the continuous multi-step reaction of metabolic pathway. In recent years, researchers proposed that the enzyme to be assembled can be anchored on the space scaffold to improve the catalytic efficiency by constructing the space scaffold structure. However, the current protein space scaffolds are all exogenous and expressed in the form of plasmids, resulting in heavy metabolic burden of cells, and the plasmid may be lost in the course of passage, and the production process is unstable. Therefore, it is a key problem in metabolic engineering field to design and construct three-dimensional protein space scaffolds with low metabolic burden and stable production process for assembling pathway enzymes in space.

SUMMARY OF THE INVENTION

In order to solve the above technical problems, the invention designs and constructs a three-dimensional scaffold with small metabolic burden and stable production process to assemble intermediate enzymes by using macromolecular structural substances of microorganism cells themselves. The invention uses the functional membrane microdomain of *Bacillus subtilis* cells as a space scaffold, and anchors the enzyme on the space scaffold by using scaffold proteins FloA and FloT, located in the functional membrane microdomain membrane raft, and the problems that the existing protein scaffolds increase the metabolic burden of cells and cause instability in the production process are solved. Compared with the recombinant bacteria without enzyme anchoring on the space scaffold, the fermentation yield of acetyl glucosamine in the invention was greatly increased The first object of the invention is to provide a recombinant *Bacillus Subtilis*, which is obtained by, using functional membrane microdomains (FMMs) of *Bacillus subtilis* itself as a space scaffold, fusing two key enzymes of acetyl glucosamine synthesis pathway, glucosamine 6-phosphate synthase (GlmS) and glucosamine 6-phosphate acetylase (GNA1) with scaffold proteins FloT and FloA in the functional membrane microdomain, respectively.

In an embodiment of the invention, the nucleotide sequence of the coding gene of the scaffold protein FloT is shown in NCBI-Gene ID: 937138.

In an embodiment of the invention, the nucleotide sequence of the coding gene of the scaffold protein FloA is shown in NCBI-Gene ID: 937865.

In an embodiment of the invention, the recombinant *Bacillus subtilis* uses *Bacillus subtilis* BSGN6 as the original strain.

In an embodiment of the invention, In the *Bacillus subtilis* BSGN6, nagP, gamP, gamA, nagA, nagB, ldh, pta and other genes are knocked out ("Liu Y., Zhu, Y., Li, J., Shin, H. D., Chen, R. R., Du, G., Liu, L. & Chen, J. Modular pathway engineering of *Bacillus subtilis* for improved N-acetylglucosamine production. Metabolic engineering 2014, 23: 42-52.)

In an embodiment of the invention, the nucleotide sequence of the encoding gene of the glucosamine-6-phosphate synthetase is shown in NCBI-Gene ID: 938736.

In an embodiment of the invention, the nucleotide sequence of the encoding gene of the glucosamine-6-phosphate acetylase is shown in NCBI-Gene ID: 179437.

In an embodiment of the invention, the nucleotide sequence of a linker connected between the glucosamine 6-phosphate synthase and the scaffold protein FloT is shown in SEQ ID NO.1.

In an embodiment of the invention, the nucleotide sequence of a linker connected between the glucosamine 6 phosphate acetylase and the scaffold protein FloA is shown as SEQ ID NO.1.

The second object of the invention is to provide a method for constructing a space scaffold-multienzyme complex, wherein functional membrane microdomains (FMMs) of *Bacillus subtilis* itself are utilized as a space scaffold, and the key enzymes to be expressed are fixed on FMMs by means of the scaffold proteins FloA and FloT (for example, SPFH domain of FloT). The key enzymes play a role during the metabolic process of acetylglucosamine.

In a preferable embodiment, the key enzymes are selected from the group consisting of glucosamine 6-phosphate synthase GlmS and glucosamine 6-phosphate acetylase GNA1, GlcNAc dephosphatase (YqaB) and Phosphoglucose isomerase (Pgi).

The third object of the invention is to provide a construction method of the recombinant *Bacillus subtilis*, and the method comprises the following steps: (1) constructing the recombinant FloT-GlmS fusion fragment, and integrating the recombinant FloT-GlmS fusion fragment into the floT locus or the glms locus of the *Bacillus Subtili*, to obtain the recombinant *Bacillus subtilis* which expresses FloT-GlmS; (2) constructing the recombinant FloA-GNA1 fusion fragment, and integrating the recombinant FloA-GNA1 fragment into the floA locus of the recombinant *Bacillus subtilis* genome of step (1), to obtain the recombinant *Bacillus subtilis* co-expressing FloA-GNA1 and FloT-GlmS.

The fourth object of the invention is to provide the use of the recombinant *Bacillus subtilis* in fermentation and production of acetyl glucosamine, and the recombinant *Bacillus subtilis* is used as the production strain to produce acetyl glucosamine.

In an embodiment of the invention, the use comprises the steps of: the recombinant *Bacillus subtilis* is activated in a seed medium, and then the activated recombinant *Bacillus subtilis* is transferred into a fermentation medium for fermentation culture to obtain acetylglucosamine.

In an embodiment of the invention, the recombinant *Bacillus subtilis* is activated in a seed medium at 35-38° C. and the activated recombinant *Bacillus Subtilis* are fermented at 35-38° C.

In an embodiment of the invention, the seed medium includes the following components: peptone, yeast powder and sodium chloride.

In a preferable embodiment of the invention, the seed medium includes the following components by weight: 5-15 $g \cdot L^{-1}$ peptone, 5-10 $g \cdot L^{-1}$ yeast powder and 5-15 $g \cdot L^{-1}$ sodium chloride.

In an embodiment of the invention, the fermentation medium comprises the following components: glucose, peptone, yeast powder, ammonium sulfate, potassium hydrogen phosphate, potassium dihydrogen carbonate, calcium carbonate and trace element solution.

In a preferable embodiment of the invention, the fermentation medium includes the following components by weight: 30-60 $g \cdot L^{-1}$ glucose, 5-8 $g \cdot L^{-1}$ peptone, 10-15 $g \cdot L^{-1}$ yeast powder, 5-8 $g \cdot L^{-1}$ ammonium sulfate, 10-15 $g \cdot L^{-1}$ potassium hydrogen phosphate, 2-3 $g \cdot L^{-1}$ potassium dihydrogen phosphate, 4-6 $g \cdot L^{-1}$ calcium carbonate and 8-12 $ml \cdot L^{-1}$ trace element solution.

In an embodiment of the invention, trace element solution includes manganese sulfate, cobalt chloride, sodium molybdate, zinc sulfate, aluminium chloride, copper chloride, boric acid and hydrochloric acid.

In a preferable embodiment of the invention, the trace element solution includes the following components: 0.8-1.2 $g \cdot L^{-1}$ manganese sulfate, 0.2-0.6 $g \cdot L$ cobalt chloride, 0.1-0.3 $g \cdot L^{-1}$ sodium molybdate, 0.1-0.3 $g \cdot L^{-1}$ zinc sulfate, 0.1-0.3 $g \cdot L^{-1}$ aluminium chloride, 0.1-0.3 $g \cdot L^{-1}$ copper chloride, 0.04-0.06 $g \cdot L^{-1}$ boric acid and 3-8 $mol \cdot L^{-1}$ hydrochloric acid.

In an embodiment of the invention, the activated seeds are cultured in fermentation medium at an inoculum size of 5-15%.

By means of the above technical solutions, the invention has the following advantages as compared with the prior art: in the invention, the FMMs of the cell itself are used a space scaffold, a multienzyme complex is designed and constructed by means of its specific marker proteins (scaffold proteins) FloA and FloT, such that the artificial substrate passage is built, and the metabolic burden of cells can be effectively reduced. Furthermore, the multienzyme complex is attached to the plasma membrane, and this will facilitate the transportation of a product from the inside of the cell to the outside. The recombinant *Bacillus subtilis* constructed by the invention can efficiently synthesize GlcNAc without affecting cell life activity, and can also limit the toxic intermediate metabolite GlcN-6-P near the plasma membrane to reduce or eliminate its inhibition on cell activity. During shaking flask fermentation using complex medium, the yield of acetyl glucosamine of the control strain BSG-C was only 0.45 $g \cdot L^{-1}$, while that of BSG-AT, BSG-ATP, BSG-ATPB increased to 5.29 $g \cdot L^{-1}$, 6.22 $g \cdot L^{-1}$ and 8.48 $g \cdot L^{-1}$ respectively. The construction method of recombinant *Bacillus subtilis* is simple, easy to use and has a good application prospect.

DETAILED DESCRIPTION OF THE PREFERRED EMBODIMENTS

The invention will be further illustrated in more detail with reference to the accompanying drawing. It is noted that, the following embodiments only are intended for purposes of illustration and are not intended to limit the scope of the invention.

Embodiment 1

Verification of FMMs of *Bacillus subtilis* as a Stable Space Scaffold

Based on *Bacillus subtilis* BSGN6, a fusion gene expression cassette of FloT and green fluorescent protein EGFP was integrated at the floT site (NCBI-Gene ID: 937138) of scaffold protein coding gene of *Bacillus subtilis* BSGN6 genome. An integration site floT sequence (1 kb in length, the C-terminal termination codon being removed), an EGFR gene sequence (0.7 kb in length, the nucleotide sequence being shown as SEQ ID NO.2), a zeocin resistant gene (the nucleotide sequence being shown as SEQ ID NO.3), and a FloT downstream (1 kb in length) were used to construct the integration cassette. The amplified FloT-EGFP fusion expression cassette was transformed into the strain BSGN6 by homologous recombination, and transformants were selected on LB plate with zeocin. Positive transformants with FloT-EGFP fusion expression were further verified by colony PCR with primers FloT-EGFP-F (GCTGA-TATCGCAACAGCAGAG)/FloT-EGFP-R (CAT-TGTCGCTTTCGCAGCAAT), and the recombinant *Bacillus subtilis* expressing FloT-EGFP was successfully obtained.

The recombinant strains expressing FloT-EGFP were mounted on a glass slide and observed under a VA-TIRFM equipped with a 100×oil-immersion objective (numerical aperture=1.45, Olympus), and the FloT-EGFP proteins were excited with 488-nm laser line from a diode laser (Changchun New Industries Optoelectronics Technology) and the emission fluorescence with a filter (BA510IF (525/50) was obtained. Finally, the images were acquired with 300 msec exposure times and a time-lapse series of single particles of FloT-EGFP was taken with up to 100 images per sequence.

Figure 1:
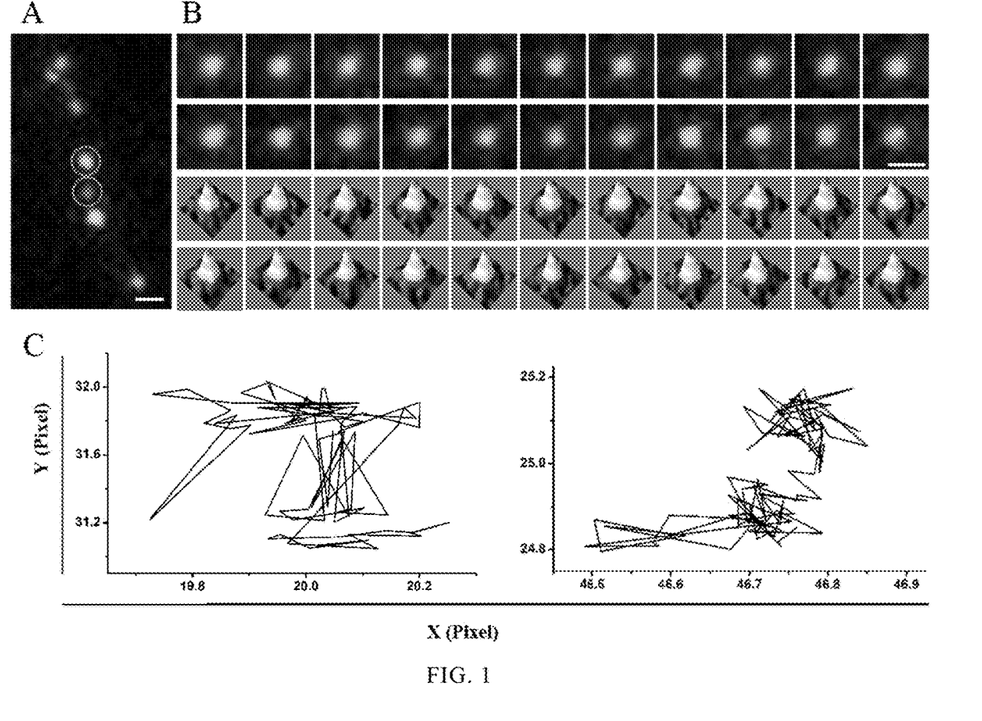
FIG. 1 shows the distribution and dynamic behaviors of FMMs labeled by FloT-EGFP at the plasma membrane, wherein (A) shows a single total internal reflection fluorescent microscope (TIRFM) for FloT-EGFP at the plasma membrane, Bar=300 nm; (B) shows a time series plot of dynamic analysis and three-dimensional fluorescence image of fluorescence spot shown in the first white circle of (A), Bar=500 nm; (C) The trajectories of fluorescence spots shown in the white circles of (A).

As shown in FIG. 1, FloT-EGFP fluorescent spots occurred as discreet spots with almost constant fluorescence, instead of distributing uniformly in the plasma membrane (FIG. 1A), and stayed at the plasma membrane during the entire observation period (FIG. 1B). The dynamic properties of FMMs were studied in more detail using single-particle tracking (SPT) in continuous images and found that all the FMMs oscillated only in the range of 2×2 pixels (FIG. 1C). All the results indicated that the observed FMMs represented stable structures with lateral and temporal stability and can be served as the stable space scaffolds.

Embodiment 2

Verification of *Bacillus subtilis* Scaffold Protein FloA and FloT Located in the Same FMMs Based on *Bacillus subtilis* BSGN6, a fusion gene expression cassette of FloA and green fluorescent protein EGFP was integrated at the floA site (NCBI-Gene ID: 937865) of scaffold protein coding gene of *Bacillus subtilis* BSGN6 genome. An integration site floA sequence (1 kb in length, the C-terminal termination codon being removed), an EGFR gene sequence (0.7 kb in length, the nucleotide sequence being shown as SEQ ID NO.2), a chloromycetin resistant gene (the nucleotide sequence being shown as SEQ ID NO.4), and a FloA downstream (1 kb in length) were used to construct the integration cassette. The amplified FloA-EGFP fusion expression cassette was transformed into the strain BSGN6 by homologous recombination, and transformants were selected on LB plate with chloromycetin. Positive transformants with FloA-EGFP fusion expression were further verified by colony PCR with primers FloA-EGFP-F (GCCTGTAATGCTTTGGATTTCA)/FloA-EGFP-R (CGTCAATTCAAGCTGGAC CTTA), and the recombinant *Bacillus subtilis* expressing FloA-EGFP was successfully obtained.

Based on the recombinant *Bacillus subtilis* with FloA-EGFP fusion, the fusion gene expression cassette of FloT and red fluorescent protein mCherry was integrated at the floT site (NCBI-Gene ID: 937138) of scaffold protein coding gene of FloA-EGFP fusion genome. An integration site floT sequence (1 kb in length, the C-terminal termination codon being removed), a mCherry gene sequence (0.7 kb in length), a zeocin resistant gene, and a FloT downstream (1 kb in length) were used to construct the integration cassette. The amplified FloT-mCherry fusion expression cassette was transformed into the *Bacillus subtilis* with FloA-EGFP fusion, and transformants were selected on LB plate with zeocin. Positive transformants with FloA-EGFP fusion and FloT-mCherry fusion expression were further verified by colony PCR with primers FloT-mCherry-F (ATCGCAACAGCAGAGGCTG)/FloT-mCherry-R (TTCGCAGCAATCGGCATAAG).

The recombinant strains co-expressing FloA-EGFP and FloT-mCherry were mounted on a glass slide and observed under a VA-TIRFM equipped with a 100×oil-immersion objective (numerical aperture=1.45, Olympus). The FloA-EGFP and FloT-mCherry were excited with 488- and 561-nm laser lines, respectively, from a diode laser (Changchun New Industries Optoelectronics Technology) and their emission fluorescence was obtained with a filter (BA510IF (525/50) for GFP; HQ605/52 for mCherry). Finally, the images were acquired with 300 msec exposure times and a time-lapse series of single particles of FloA-EGFP/FloT-mCherry was taken with up to 200 images per sequence.

Figure 2:
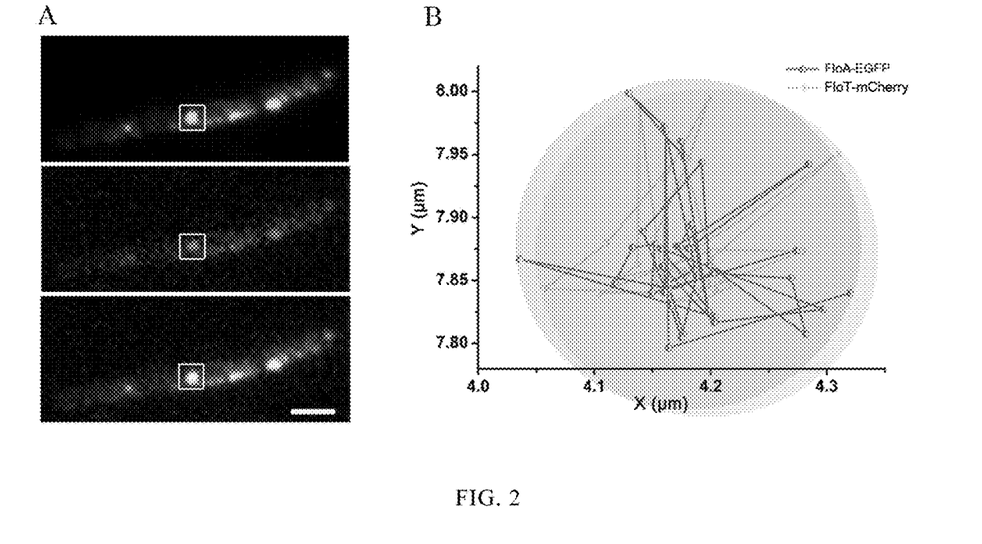
FIG. 2 shows the correlation between scaffold proteins FloA and FloT, wherein (A) VA-TIRFM images of the cells co-expressing FloA-EGFP and FloT-mCherry, Bar=1 μm. (B) The trajectories of fluorescence spots FloA-EGFP and FloT-mCherry shown in white circles in (A).

Cells co-expressing FloA-EGFP and FloT-mCherry under the control of native promotors were imaged by dual-color VA-TIRFM. Excitation was switched between two lasers so that the cells were alternatively illuminated with blue (473 nm) and green (561 nm) light, and a continuous video frames were obtained. When two consecutive frames representing green and red fluorescence were overlaid, we detected some yellow regions caused by the high intensity in both the green and red channels, suggesting an overlap of the FloA-EGFP and FloT-mCherry fluorescent spots (FIG. 2A). At the same time, FloA was found to co-diffused with FloT during observation time, and the lateral diffusion trajectories of the overlapped fluorescent spot were shown in FIG. 2B. All the observations showed that FloA and FloT were located in the same FMMs, which could be selected as the skeleton of subsequent multiple enzyme complexes.

Embodiment 3

Verify that the SPFH domain was responsible for FMMs location

Figure 3:
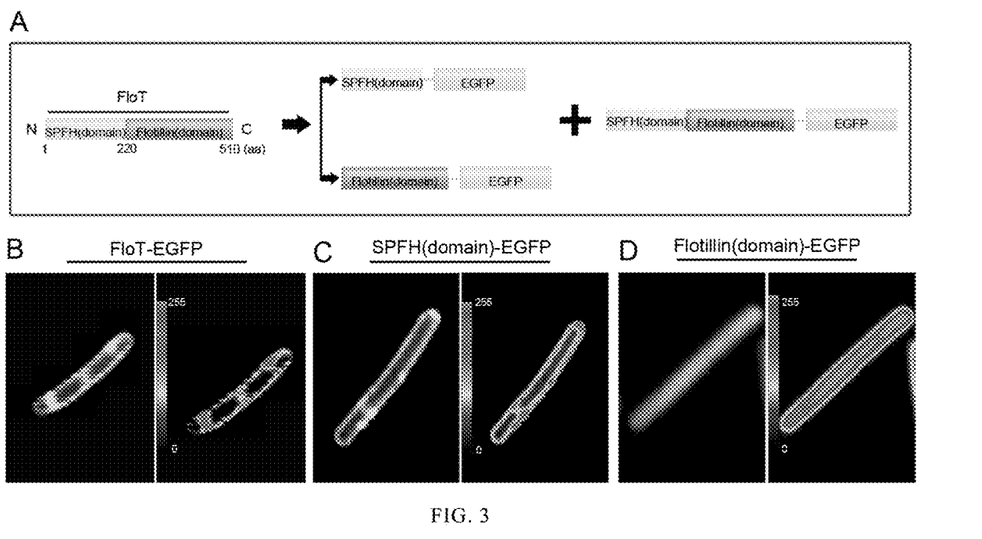
FIG. 3 shows the localization analysis of different domains of FloT protein: (A), sketch map of fusion expression of different domains and EGFP; (B-D), the confocal images of the full length FloT (B), SPFH domain (C) and flotillin domain (D).

It was known that flotillin-like scaffold proteins generally consist of two domains, the N-terminal SPFH domain and the C-terminal flotillin domain. To identify which domain is responsible for protein localization, the sequence of FloT protein was divided into SPFH domain (1-220 aa) and flotillin domain (221-510 aa) by bioinformatics analysis and the strains expressing a C-terminal EGFP fusion to the full length FloT, SPFH domain and flotillin domain were generated using the pP43NMK plasmid. As shown in FIG. 3, laser scanning confocal microscopy and fluorescence intensity 3D analysis revealed that the fluorescence signal of SPFH domain was mainly located at the plasma membrane, similar to that of full length FloT, suggesting that the SPFH domain of FloT is responsible for protein localization to FMMs.

Embodiment 4

Construction of Recombinant *Bacillus subtilis* BSG-AT

Based on *Bacillus subtilis* BSGN6, a fusion gene expression cassette of FloT and Glcn-6-p synthase encoding gene glms was integrated at the floT site (NCBI-Gene ID: 937138) of scaffold protein coding gene of *Bacillus subtilis* BSGN6 genome. An integration site floT sequence (1 kb in length, the C-terminal termination codon being removed), a glmS gene sequence (1.8 kb in length) with a (GGGGS) 3 linker at N-terminal, a chloramphenicol resistant gene CmR and a FloT downstream sequence (1 kb in length) were used to construct the FloT-GlmS fusion gene integration cassette. By homologous recombination, the integrated cassette was integrated into the genome of *Bacillus subtilis* BSGN6. The recombinant *Bacillus subtilis* expressing FloT-GlmS was obtained by screening of chloramphenicol resistance plate, colony PCR validation and sequencing. The recombinant *Bacillus subtilis* expressing FloT-GlmS was successfully integrated, and chloramphenicol resistance was eliminated.

Based on the above recombinant *Bacillus subtilis* with resistance knockout, a fusion gene expression cassette of FloA and Glcn-6-p acetylase gene GNA1 was integrated at the floA site (NCBI-Gene ID: 937865) of scaffold protein coding gene of *Bacillus subtilis* BSGN6 genome. An integration site floA sequence (1 kb in length, the C-terminal termination codon being removed), a GNA1 gene sequence (0.5 kb in length) with (GGGGS) 3 linker at N-terminal, a chloramphenicol resistant gene CmR and a FloA downstream sequence (1 kb in length) were used to construct the FloA-GNA1 fusion gene integration cassette. By means of homologous recombination, the above integrated cassette was integrated into the recombinant *Bacillus subtilis* of FloT-GlmS. The recombinant *Bacillus subtilis* co-expressing FloA-GNA1 and FloT-GlmS was obtained by screening of chloramphenicol resistant plate, colony PCR validation and sequencing. The recombinant *Bacillus Subtilis* co-expressed with FloA-GNA1 and FloT-GlmS was successfully synthesized, and the strain BSG-AT was finally obtained by resistance knockout.

Using a similar method as mentioned above, only the C-terminal termination codon of the integration site floT sequence and the integration site floA sequence were not deleted, the FloT (TAA) -GlmS and FloA (TAA) -GNA1 non-fusion gene integration cassette were constructed, and the control strain BSG-C was obtained by the similar method.

Embodiment 5

Construction of Recombinant *Bacillus subtilis* BSG-ATP and BSG-ATPB

Phosphoglucose isomerase (Pgi) was immobilized into FMMs by the fusion expression of SPFH-pgi driven by pgi endogenous promoter in BSG-AT strain, resulting the strain BSG-ATP in which GNA1, GlmS and Pgi (NCBI-Gene ID: 937165) were all immobilized into FMMs simultaneously.

Figure 4:
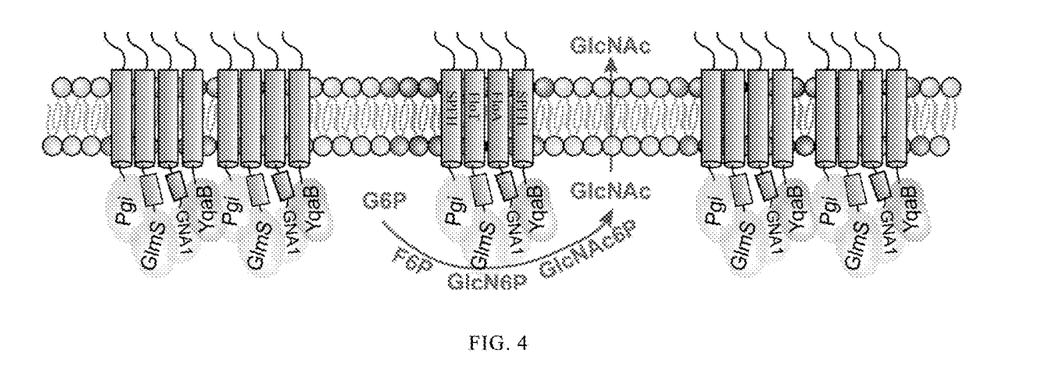
FIG. 4 shows the schematic diagram of the distribution of enzymes required for GlcNAc synthesis in BSG-ATPB strains.

Further immobilization of exogenous GlcNAc dephosphatase (YqaB) from *Escherichia coli*, which can participate in the process of GlcNAc6P dephosphorylation into FMMs of the BSG-ATP to obtain the strain BSG-ATPB, in which the GNA1, GlmS, Pgi, and YqaB were all located in FMMs. Schematic diagram of the distribution of enzymes required for GlcNAc synthesis in BSG-ATPB strains was shown in FIG. 4.

Embodiment 6

Fermentation production of Acetylglucosamine by Recombinant *Bacillus Subtilis*

Figure 5:
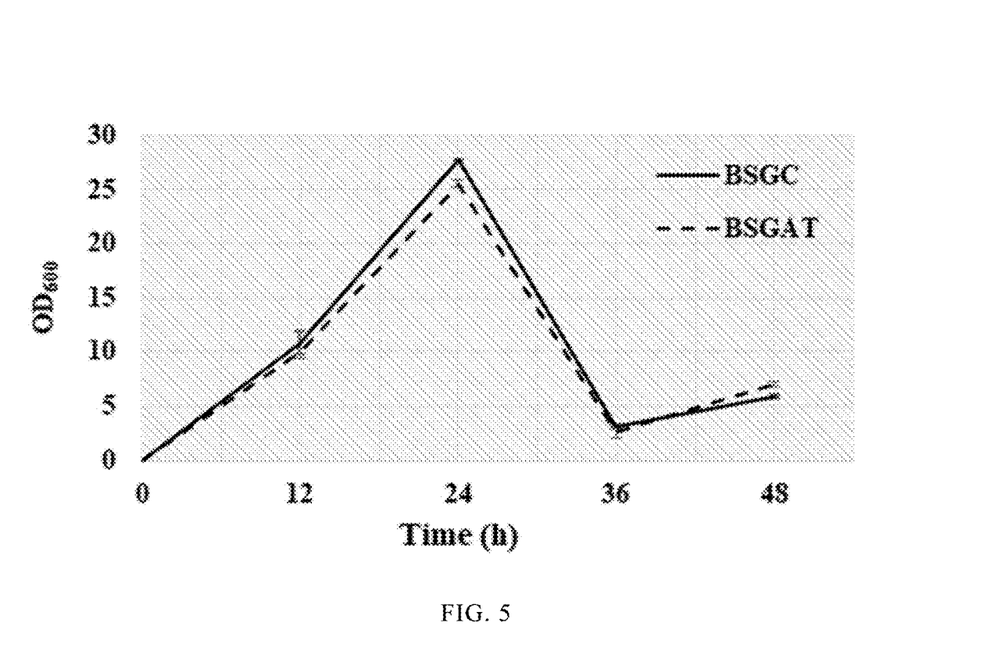
FIG. 5 shows the comparison of cell growth of the strains BSG-AT and BSG-C during fermentation.

To determine the effects of FMM-GNA1-GlmS complex system on cell growth, the strains BSG-AT and BSG-C were inoculated with an inoculum size of 5% (v/v) into 250-mL shake flasks each containing 25 mL of fermentation medium. And then, fermentation was carried out at 220 rpm and 37° C. for 48 h on rotary shakers. It could be seen from FIG. 5 that the FMM-GNA1-GlmS complex system had little influence on cell growth which was calculated by the optical density at 600 nm (OD600), indicating that this space scaffold system has no obvious metabolic burden on cells.

Shake-flask fermentation of the strains BSG-AT and BSG-C:

The seed medium was Luria-Bertani broth or agar plates containing (g·L$^{-1}$): tryptone 10, yeast extract 5, and NaCl 10. The fermentation medium contained (g·L$^{-1}$): tryptone 6, yeast extract 12, $(NH_4)_2SO_4$ 6, $K_2HPO_4·3H_2O$ 12.5, $KH_2PO_4$ 2.5, $CaCO_3$ 5, glucose 60, and 10 ml of trace metal solution. The trace metal solution contained (per liter of 5M HCl) (g·L$^{-1}$): $MnSO_4·5H_2O$ 1.0, $CoCl_2·6H_2O$ 0.4, $NaMnO_4·2H_2O$ 0.2, $ZnSO_4·7H_2O$ 0.2, $AlCl_3·6H_2O$ 0.1, $CuCl_2O$ 0.1, and $H_3BO_4$ 0.05. Seed culture was carried out in 100-mL shake flasks each containing 10 mL of seed medium with shaking at 220 rpm and 37° C. for 8 h, the seed (1.25 mL) was inoculated into 250-mL shake flasks containing 25 mL of fermentation medium, and then fermentation was carried out at 220 rpm and 37° C. for 48 h on rotary shakers.

Figure 6:
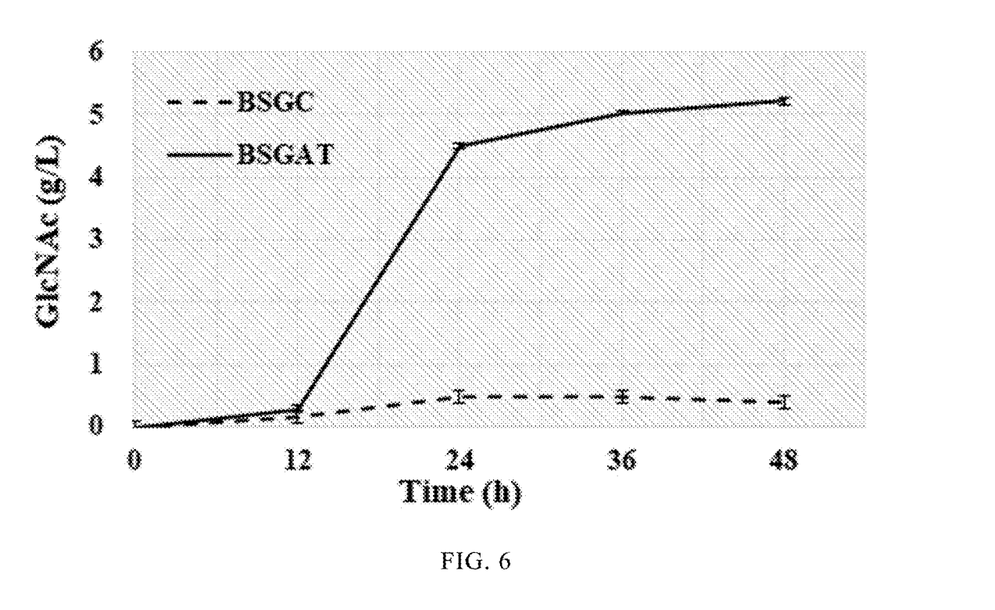
FIG. 6 shows the comparison of GlcNAc content of the strains BSG-AT and BSG-C during fermentation.
Figure 7:
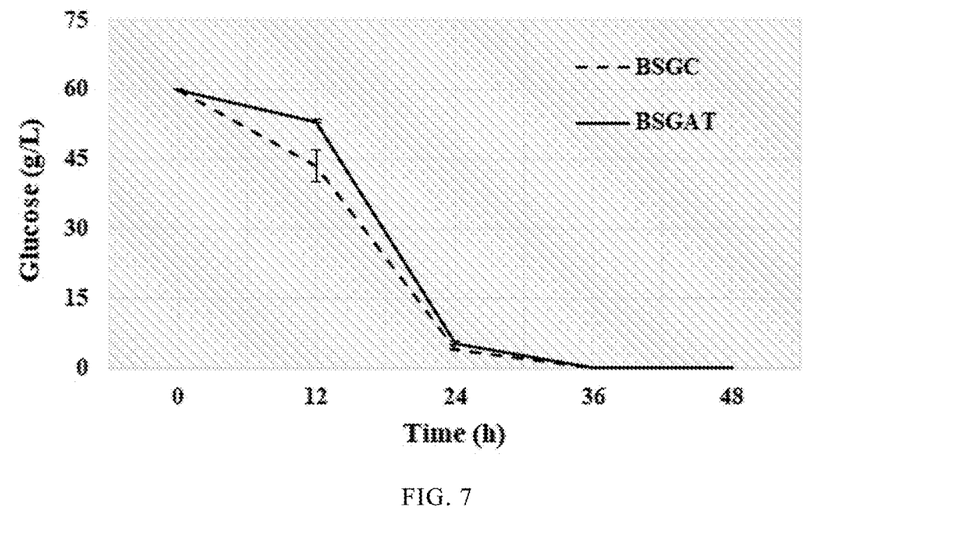
FIG. 7 shows the comparison of the residual glucose concentration of the strains BSG-AT and BSG-C during fermentation.

To determine the effects of FMM-GNA1-GlmS complex system on GlcNAc production, the strains BSG-AT and BSG-C were inoculated with an inoculum size of 5% (v/v) into 250-mL shake flasks each containing 25 mL of fermentation medium. And then, fermentation was carried out at 220 rpm and 37° C. for 48 h on rotary shakers. The yield of GlcNAc for BSG-AT was 5.29 g·L$^{-1}$. It could be seen from FIG. 6 that the strain BSG-AT produced GlcNAc to a higher concentration than BSG-C by 4.84 g·L$^{-1}$ in the flask cultivation, which was 11.76-fold of that of BSG-C. FIG. 7 showed the time profile of glucose consumption of BSG-AT and BSG-C in shake flask.

Figure 8:
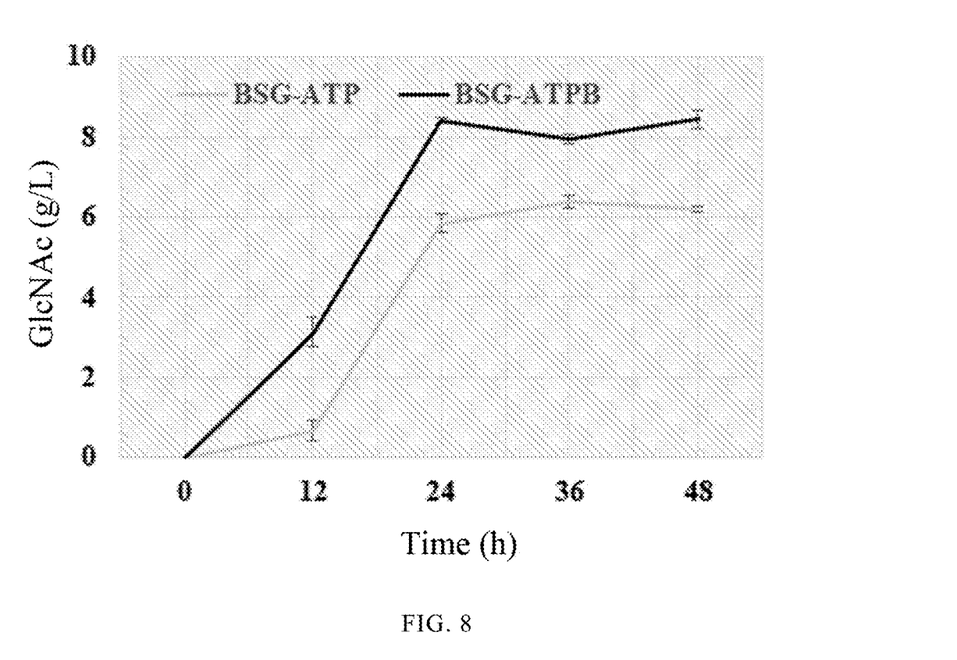
FIG. 8 shows the comparison of GlcNAc content of strains BSG-ATP and BSG-ATPB during fermentation.

The same method was used to ferment BSG-ATP and BSG-ATPB and determine the yield of GlcNAc, as shown in FIG. 8, the yield of GlcNAc of BSG-ATP in shake flask culture increased to 6.22 g·L$^{-1}$ and the yield of GlcNAc of BSG-ATPB increased to 8.48 g·L$^{-1}$.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A recombinant *Bacillus subtilis*, wherein the recombinant *Bacillus subtilis* is obtained by fusing glucosamine 6-phosphate synthase GlmS and glucosamine 6-phosphate acetylase GNA1 with scaffold protein FloT and FloA in functional membrane microdomain of *Bacillus subtilis*, respectively.

2. The recombinant *Bacillus subtilis* as claimed in claim 1, wherein the recombinant *Bacillus subtilis* is originated from *Bacillus subtilis* B SGN6.

3. The recombinant *Bacillus subtilis* as claimed in claim 1, wherein the glucosamine 6-phosphate synthase GlmS and the scaffold protein FloT are connected via a linker which is encoded by the nucleotide sequence shown in SEQ ID NO.1.

4. The recombinant *Bacillus subtilis* as claimed in claim 1, wherein the glucosamine 6 phosphate acetylase GNA1 and the scaffold protein FloA are connected via a linker which is encoded by the nucleotide sequence shown in SEQ ID NO.1.

5. A method of producing acetyl glucosamine by fermentation comprising:
providing the recombinant *Bacillus subtilis* as claimed in claim 1;
activating the recombinant *Bacillus subtilis* in a seed medium; and
transferring the activated recombinant *Bacillus subtilis* into a fermentation medium for fermentation culture to obtain acetylglucosamine.

6. The method as claimed in claim 5, wherein the seed medium includes 5-15 $g·L^{-1}$ peptone, 5-10 $g·L^{-1}$ yeast powder and 5-15 $g·L^{-1}$ sodium chloride, and the fermentation medium includes 30-60 $g·L^{-1}$ glucose, 5-8 $g·L^{-1}$ peptone, 10-15 $g·L^{-1}$ yeast powder, 5-8 $g·L^{-1}$ ammonium sulfate, 10-15 $g·L^{-1}$ potassium hydrogen phosphate, 2-3 $g·L^{-1}$ potassium dihydrogen phosphate, and 4-6 $g·L^{-1}$ calcium carbonate.

* * * * *